United States Patent
Bartling

(10) Patent No.: US 10,561,323 B2
(45) Date of Patent: Feb. 18, 2020

(54) METHOD, SYSTEM AND APPARATUS FOR MEASURING MULTIPLE SIGNALS IN A BODY

(71) Applicant: Microchip Technology Incorporated, Chandler, AZ (US)

(72) Inventor: D. Ryan Bartling, Phoenix, AZ (US)

(73) Assignee: MICROCHIP TECHNOLOGY INCORPORATED, Chandler, AZ (US)

(*) Notice: Subject to any disclaimer, the term of this patent is extended or adjusted under 35 U.S.C. 154(b) by 188 days.

(21) Appl. No.: 15/409,532

(22) Filed: Jan. 19, 2017

(65) Prior Publication Data
US 2017/0202465 A1 Jul. 20, 2017

Related U.S. Application Data

(60) Provisional application No. 62/281,071, filed on Jan. 20, 2016.

(51) Int. Cl.
*A61B 5/1455* (2006.01)
*A61B 5/024* (2006.01)
(Continued)

(52) U.S. Cl.
CPC ...... *A61B 5/02427* (2013.01); *A61B 5/02416* (2013.01); *A61B 5/02433* (2013.01);
(Continued)

(58) Field of Classification Search
CPC ............ A61B 5/725; A61B 2560/0252; A61B 2562/0233; A61B 5/02416–02433;
(Continued)

(56) References Cited

U.S. PATENT DOCUMENTS 5,807,267 A * 9/1998 Bryars ............... A61B 5/02433
600/500
5,830,137 A * 11/1998 Scharf ............... A61B 5/14551
600/323

(Continued)

FOREIGN PATENT DOCUMENTS

EP 0502717 A1 9/1992 ............... A61B 5/00

OTHER PUBLICATIONS

Feng, Zhang, "AN1525: Pulse Oximeter Design Using Microchip dsPIC® Digital Signal Controllers (DSCs) and Analog Devices," Microchip Technology Incorporated, 14 pages, Nov. 29, 2012.

(Continued)

*Primary Examiner* — Meredith Weare
(74) *Attorney, Agent, or Firm* — Slayden Grubert Beard PLLC

(57) ABSTRACT

A pulse oximetry measurement system uses a pseudo-random noise generator to stimulate one or more light emitting diodes (LEDs). The light amplitudes from these LEDs, after passing through a part of a body, are detected by a phototransistor or photodiode and digitized with an analog-to-digital converter (ADC). The digitized ADC light amplitude values are re-correlated with the outgoing pseudo-random noise stimulus. Spread spectrum techniques are known for their noise mitigation properties, and ability to pass multiple signals through the same medium without interference. Thus, these measurements can be performed substantially simultaneously with minimal interference from each other. The pulse oximetry measurement system correlates the measured light intensities using pseudo-random noise generation and phase division multiplexing, and computes the measured and correlated peak-to-peak detected light amplitudes to obtain a ratio between these light ampli- (Continued)

tudes for determining oxygen saturation in the blood, and may also be used for heart rate monitoring.

19 Claims, 8 Drawing Sheets

(51) Int. Cl.
    *A61B 5/00*        (2006.01)
    *H04B 13/00*     (2006.01)
    *G01J 1/08*        (2006.01)
    *G01J 1/44*        (2006.01)

(52) U.S. Cl.
    CPC ...... *A61B 5/14551* (2013.01); *A61B 5/14552* (2013.01); *A61B 5/7203* (2013.01); *A61B 5/7225* (2013.01); *A61B 5/7228* (2013.01); *A61B 5/7246* (2013.01); *G01J 1/08* (2013.01); *G01J 1/44* (2013.01); *H04B 13/005* (2013.01); *A61B 5/725* (2013.01); *A61B 2560/0252* (2013.01); *A61B 2562/0233* (2013.01); *G01J 2001/444* (2013.01); *G01J 2001/4413* (2013.01)

(58) Field of Classification Search
    CPC .......... A61B 5/1455–14558; G01J 1/44; G01J 1/08; G01J 2001/444; G01J 2001/4413; H04B 10/116
    See application file for complete search history.

(56) References Cited

U.S. PATENT DOCUMENTS

| | | | | |
|---|---|---|---|---|
| 5,995,858 | A * | 11/1999 | Kinast | A61B 5/14551 600/323 |
| 7,729,732 | B2 * | 6/2010 | Ohashi | A61B 5/14553 600/310 |
| 2003/0184179 | A1* | 10/2003 | Galbraith | H02K 39/00 310/166 |
| 2004/0260186 | A1* | 12/2004 | Dekker | A61B 5/0205 600/483 |
| 2005/0187451 | A1* | 8/2005 | Norris | A61B 5/14551 600/326 |
| 2009/0306487 | A1* | 12/2009 | Crowe | A61B 5/02433 600/322 |
| 2012/0088982 | A1* | 4/2012 | Rulkov | A61B 5/02438 600/301 |
| 2012/0296185 | A1* | 11/2012 | Sagan | A61B 5/14551 600/336 |
| 2014/0061442 | A1* | 3/2014 | Denham | H04N 5/37455 250/214 DC |
| 2014/0214330 | A1 | 7/2014 | Iyer et al. | 702/19 |
| 2014/0275825 | A1 | 9/2014 | Lisogurski | 600/301 |

OTHER PUBLICATIONS

International Search Report and Written Opinion, Application No. PCT/US2017/014319, 12 pages, dated Apr. 11, 2017.
European Office Action, Application No. 17702736.4, 8 pages, dated Jul. 15, 2019.

* cited by examiner (PRIOR TECHNOLOGY)

(PRIOR TECHNOLOGY)

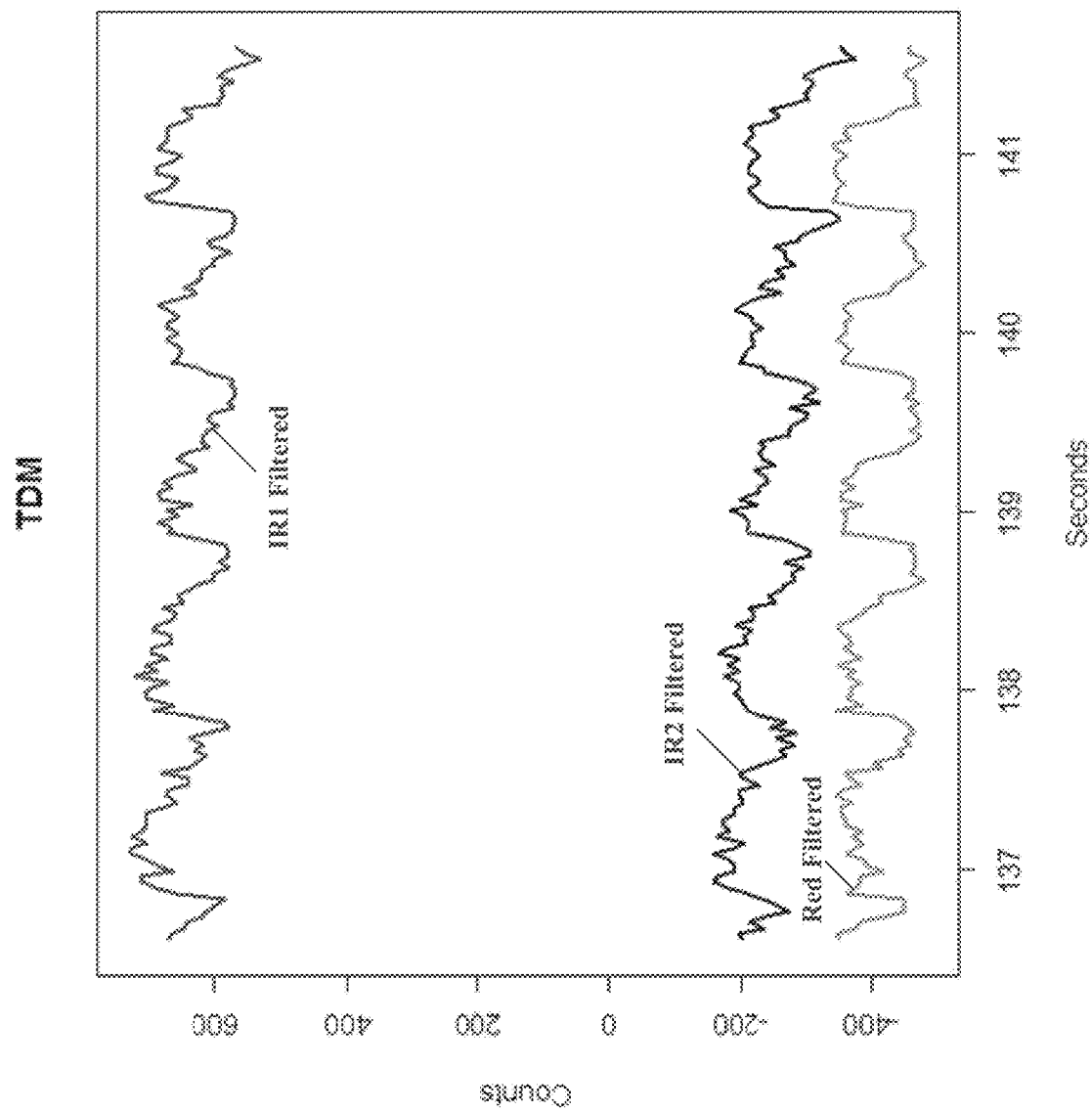
Figure 7 (Prior Technology)

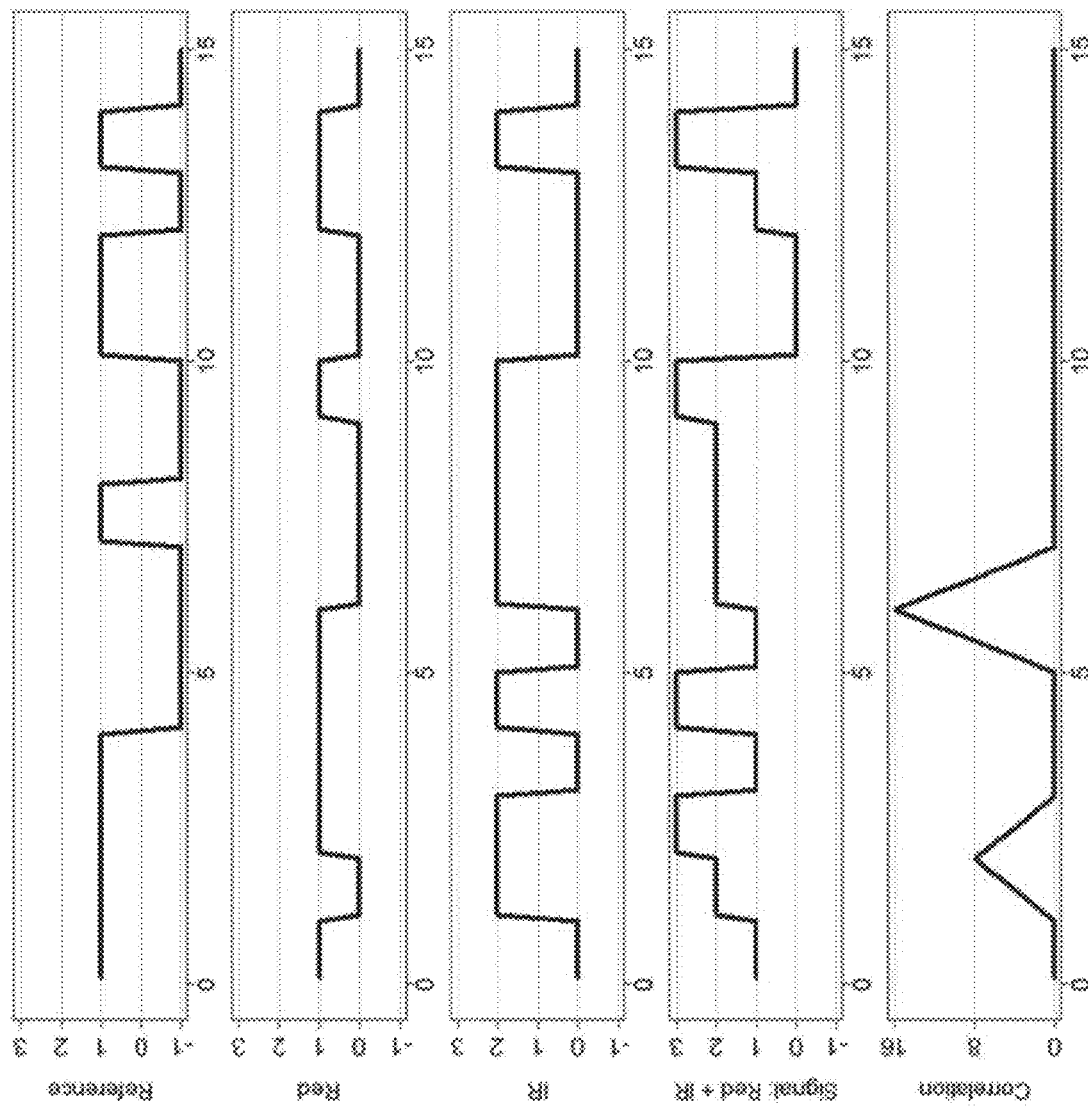

METHOD, SYSTEM AND APPARATUS FOR MEASURING MULTIPLE SIGNALS IN A BODY

RELATED PATENT APPLICATION

This application claims priority to U.S. Provisional Patent Application No. 62/281,071 filed Jan. 20, 2016; which is hereby incorporated by reference herein for all purposes.

TECHNICAL FIELD

The present disclosure relates to signal analysis, in particular, signal analysis of active sensors, e.g., pulse oximetry biometric measurements.

BACKGROUND

Certain biometric measurements are subject to noise which makes it very difficult to provide a proper analysis of the sensor signals. In particular, pulse oximetry measurements are noise sensitive. Pulse oximetry uses a pulse oximeter which is a non-invasive medical device that monitors the oxygen saturation of a patient's blood and heart rate. Referring to FIGS. 5 and 6, depicted are schematics of a general overview block diagram and a more detailed block diagram of a prior technology pulse oximetry measurement system. A pulse oximeter monitors the oxygen saturation ($SpO_2$) of a human's blood based on the red light (600-750 nm wavelength) and infrared light (850-1000 nm wavelength) absorption characteristics of oxygenated hemoglobin ($HbO_2$) and deoxygenated hemoglobin (Hb). The pulse oximeter flashes red and infrared lights, e.g., light emitting diodes (LEDs), alternately through a finger to a photodiode. $HbO_2$ absorbs more infrared light and allows more red light to pass through. On the other hand, Hb absorbs more red light and allows more infrared light to pass through. The photodiode receives the non-absorbed light from each LED. The light intensity measurements for each red and infrared light source must be taken at different times and ambient light (background light noise) will affect these measurements. Flickering lights (e.g., fluorescent lights) as a noise source are difficult to eliminate.

Operation of the circuits shown in FIGS. 5, 6 and 7 are more fully explained in Application Note AN1525, "Pulse Oximeter Design Using Microchip's Analog Devices and dsPIC® Digital Signal Controllers (DSCs)" by Zhang Feng, published 2013 by Microchip Technology Inc., available at www.microchip.com, and is hereby incorporated by reference herein for all purposes. FIG. 7 shows exemplary waveforms displaying the pulse signals from the pulse oximeter systems of FIGS. 5 and 6.

SUMMARY

Therefore a need exists for a noise immune sensor signal measurement method, system and apparatus, in particular for pulse oximetry measurements.

According to an embodiment, a system for measuring multiple signals in a body may comprise: at least one first light source generating a first color light; at least one second light source generating a second color light; at least one light sensor adapted for detecting light amplitudes, wherein the at least one first and second light sources and the at least one light sensor may be adapted for a portion of a body to be located therebetween; a pseudo-random noise generator adapted for turning on and off the at least one first and second light sources at pseudo-random times; an analog-to-digital converter (ADC) for converting sampled light amplitudes from the at least one light sensor into digital representations thereof; and a correlation circuit coupled to a digital output of the ADC and the pseudo-random noise generator, wherein the correlation circuit associates the digital representations with corresponding ones of the at least one first and second light sources.

According to a further embodiment, a digital filter may filter the correlated digital representations. According to a further embodiment, a heartbeat detection circuit may be coupled to an output of the digital filter. According to a further embodiment, a blood oxygen saturation ($SpO_2$) determination circuit may be coupled to an output of the digital filter. According to a further embodiment, the pseudo-random noise generator comprises a linear feedback shift register receiving a clock signal that generates a maximum length (ML) sequence, wherein the clock signal may also be coupled to the ADC. According to a further embodiment, the ADC may be triggered on a positive going edge of the clock signal and the pseudo-random noise generator may be triggered on a negative going edge of the clock signal. According to a further embodiment, the ML sequence may be phase shifted for each one of the light sources. According to a further embodiment, the ML sequence may be phase shifted for each one of a plurality of other sources. According to a further embodiment, the linear feedback shift register may comprise a plurality of shift registers that may be either added to or subtracted from based upon a corresponding output of the pseudo-random noise generator.

According to a further embodiment, may comprise: at least one first digital-to-analog converter (DAC) having an analog output coupled to the at least one first light source; and at least one second digital-to-analog converter (DAC) having an analog output coupled to the at least one second light source; wherein the at least one first and second DACs control light intensities of the first and second light sources. According to a further embodiment, the first color light may be at substantially a red wavelength and the second color light may be at substantially an infrared wavelength. According to a further embodiment, the first color light may be at substantially a green wavelength and the second color light may be at substantially a yellow-green wavelength. According to a further embodiment, digital representations of ambient light samples may be subtracted from the digital representations of the sampled light amplitudes from the at least one first and second light sources. According to a further embodiment, interfaces for the at least one first and second light sources and the at least one light sensor, the pseudo-random noise generator, ADC, and correlation circuit may be provided by a microcontroller. According to a further embodiment, a communications interface may be coupled to the microcontroller and may provide oxygen saturation and heartbeat information. According to a further embodiment, the at least one first and second light sources may comprise light emitting diodes (LEDs) and the at least one light sensor may comprise at least one photo-diode or photo-transistor.

According to an embodiment, a method for measuring multiple signals in a body may comprise the steps of: generating a first color light with at least one first light source; generating a second color light with at least one second light source; detecting light amplitudes with at least one light sensor, wherein the at least one first and second light sources and the at least one light sensor may be adapted for a portion of a body to be located therebetween; turning on and off the at least one first and second light sources at pseudo-random times generated by a pseudo-random noise generator; converting sampled light amplitudes from the at least one light sensor into digital representations thereof with an analog-to-digital converter (ADC); and correlating the digital representations of the sampled light amplitudes with corresponding ones of the at least one first and second light sources using the pseudo-random times from the pseudo-random noise generator.

According to a further embodiment of the method, may comprise the step of filtering the correlated digital representations with a digital filter. According to a further embodiment, the step of determining oxygen saturation ($SpO_2$) of blood from the digital may be representations of the sampled light amplitudes. According to a further embodiment of the method, may comprise the step of phase shifting the pseudo-random times from the pseudo-random noise generator.

According to an embodiment, a microcontroller configured for measuring multiple signals in a body may comprise: at least one first driver for turning on and off at least one first light source generating a first color light; at least one second driver for turning on and off at least one second light source generating a second color light; at least one analog input for receiving an output from at least one light sensor adapted for detecting light amplitudes, wherein the at least one first and second light sources and the at least one light sensor may be adapted for a portion of a body to be located therebetween; a pseudo-random noise generator coupled to the at least one first and second drivers for turning on and off the at least one first and second light sources at pseudo-random times; an analog-to-digital converter (ADC) for converting sampled light amplitudes received from the at least one light sensor into digital representations thereof; and a correlation circuit coupled to a digital output of the ADC and the pseudo-random noise generator, wherein the correlation circuit associates the digital representations with corresponding ones of the at least one first and second light sources.

According to a further embodiment, may comprise: at least one first digital-to-analog converter (DAC) coupled to at least one first analog output adapted for coupling to the at least one first light source; and at least one second digital-to-analog converter (DAC) coupled to at least one second analog output adapted for coupling to the at least second first light source; wherein the at least one first and second DACs control intensities of the first and second color lights.

BRIEF DESCRIPTION OF THE DRAWINGS

A more complete understanding of the present disclosure may be acquired by referring to the following description taken in conjunction with the accompanying drawings wherein:

FIG. 7 illustrates exemplary waveforms of the prior technology pulse oximetry measurement systems shown in FIGS. 5 and 6; and FIG. 8 illustrates a schematic graphical plot of a ML sequence used to generate the red and IR signals, according to the teachings of this disclosure.

Figure 1:
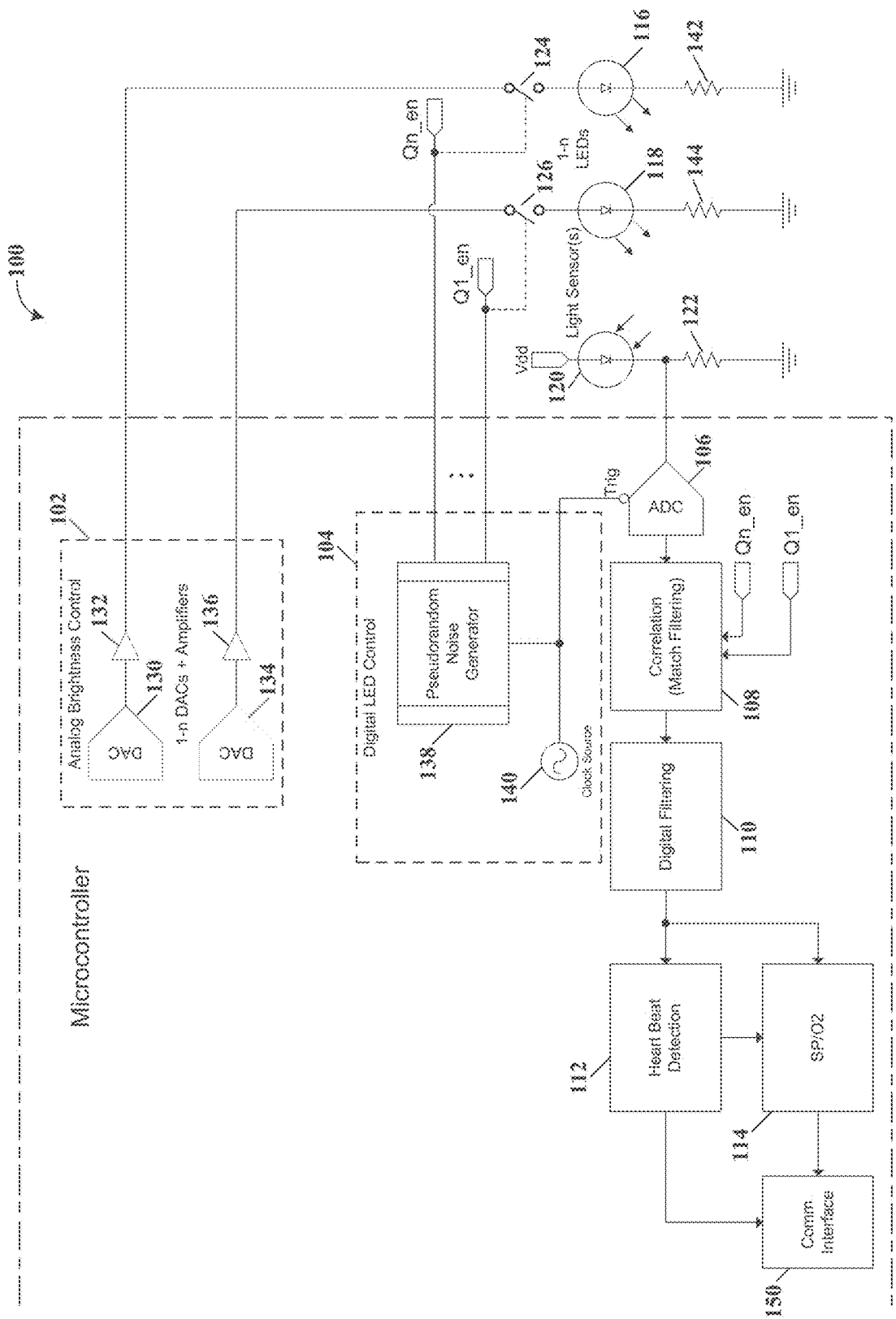
FIG. 1 illustrates a schematic block diagram of a pulse oximetry measurement system using PDM, according to a specific example embodiment of this disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein.

DETAILED DESCRIPTION

According to various embodiments of this disclosure, a pulse oximetry measurement system uses a pseudo-random noise (PN) generator to stimulate one or more light emitting diodes (LEDs). The light amplitudes from these LEDs, after passing through a part of a body, are detected by a phototransistor or photodiode and digitized with an analog-to-digital converter (ADC). The digitized light amplitude values are then re-correlated with the outgoing pseudo-random noise stimulus using phase division multiplexing. Spread spectrum techniques are known for their noise mitigation properties, and ability to pass multiple signals through the same medium without interference. Thus, these measurements can be performed on two or more LEDs with minimal interference from each other.

One problem faced by sensors utilizing a plurality of signal sources (LEDs in the case of the pulse oximeter) is like that faced by communications systems that have many users. Each LED must share the same sensor (photodiode). This is typically done by turning on each light source in sequence, and then taking each measurement in turn. So, each source gets its own slice of time in which the sensor can get its measurement. This is called time-division multiplexing (TDM). The chief drawback to using TDM is that adding more sensors, while keeping all else the same, requires more time to get measurements from every source, reducing the overall sample rate for each source. Also, since the signal you're trying to measure (arterial pulsation) is a changing signal, the measurements are biased by the order in which they were taken. A high sample rate can help reduce both concerns, but the last concern is that current techniques require a background measurement to be subtracted from the source measurements.

The method that many wireless applications have arrived at is to use code division multiple access (CDMA). In this technique, systems use coded sequences (e.g., gold codes) that have a very low cross-correlation between each other. This allows multiple users of the spectrum to coexist simultaneously with very little cross-talk between codes. In digital systems, that minimal amount of cross-talk can be discarded easily, but it is enough to cause issues when trying to take precise analog measurements. According to the teachings of this disclosure, a pulse oximeter may use a maximal length (ML) sequence, (maximal length sequences can also be used to generate gold codes) but instead of using multiple sequences like in CDMA, only one sequence is required and may be phase shifted for each LED source. This will be referred to hereinafter as "phase division multiplexing (PDM)", and works because of certain properties of ML sequences.

A ML sequence gets its name because it represents the maximum number of (non-zero) states that can be represented by a given number of bits. For example, given 4-bits, the sequence will repeat after every 15 (2n−1) states or "chips". Thus, there's almost an equal number of 1s, and 0s in every ML sequence (exactly one fewer 0s than 1s). By convention, the 0's may be treated as −1's. This causes the circular auto-correlation of the sequence to peak at 15 (again, 2n−1) when lined up. That should be trivial to see, since every multiplication is either 1×1 or −1×−1 and so you just sum up the 15 results to get 15. What is significant is that the off-peak response is a flat −1 for the entire correlation function. This means that if the same sequence is repeated and shifted, the constituent signals may be separated by using correlation.

This property is illustrated in FIG. 8. The plot at the top shows the ML sequence. The ML sequence is shifted to generate the "red", and "IR" signals. The ADC 106 sees the combined signal, and the final plot shows the circular cross-correlation between the reference, and the signal. The two peaks line up with the phase shifts for the red, and IR signals. The correlation for all other phase offsets is zero. This means another 13 sensor sources could be slotted in without impacting the measurement period or the results of the other two sources. That represents a significant advantage over traditional TDM methods.

ML sequences may be generated using Linear Feedback Shift Registers (LFSRs). These can be implemented in either hardware or software. LFSRs can be made using any length of shift register of three or more flip-flops, and XORing the outputs of a set of flip-flops back to the input of the shift register. Table 1 below provides a selection of valid LFSR parameters. An LFSR may have multiple taps, and there will always be at least two tap options for any given size. The LFSR configuration used in FIG. 2 may be constructed using configurable logic cells (CLCs) 238.

| Size (n) | Taps | Sequence Length (k) |
|---|---|---|
| 3 | 2 | 7 |
| 4 | 3 | 15 |
| 5 | 3 | 31 |
| 6 | 5 | 63 |
| 7 | 6 | 127 |
| 8 | 4, 5, 6 | 255 |
| 9 | 5 | 511 |
| 10 | 7 | 1023 |

Typically, conventional reflectance pulse oximetry uses two light wavelengths, Red and Infrared (IR). Alternatively, Green and Yellow-Green may be used. The heart rate of the person wearing the light sensor may also be determined from the signals received therefrom. According to the teachings of this disclosure, a pulse oximetry measurement system correlates the measured light intensities with a pseudo-random noise (PN) generator, and may then compute the measured and correlated peak-to-peak detected light amplitudes to obtain a ratio between these light amplitudes for determining oxygen saturation in the blood.

In comparison to the proposed solution disclosed herein, prior technology pulse oximetry measurement systems lack of randomization of measurement sequences leads to measurement bias. Flickering lights (e.g., fluorescent lights) as a noise source are difficult to eliminate. Movement presents difficulty in measuring heartbeat or SP/O$_2$. No consumer wrist or touch oximeters are available yet.

Referring now to the drawings, the details of example embodiments are schematically illustrated. Like elements in the drawings will be represented by like numbers, and similar elements will be represented by like numbers with a different lower case letter suffix.

Referring now to FIG. 1, depicted is a schematic block diagram of a pulse oximetry measurement system using phase division multiplexing (PDM), according to a specific example embodiment of this disclosure. The pulse oximetry measurement system using PDM, generally represented by the numeral 100, may comprise analog brightness control 102, digital LED control 104, an analog-to-digital converter (ADC) 106, a correlation circuit (match filtering) 108, digital filtering 110, e.g., finite impulse response (FIR) and/or infinite impulse response (IIR) filters; heartbeat detection 112, and oxygen saturation determination (SpO$_2$) 114. The aforementioned elements may be provided with an analog/digital mixed signal integrated circuit, e.g., a microcontroller. The pulse oximetry measurement system 100 may further comprise at least one red light source (e.g., Red LED) 116, at least one infrared light source (e.g., IR LED) 118, at least one light sensor (e.g., photodiode, phototransistor) 120, a current sensing resistor 122, and switches 124 and 126, e.g., metal oxide semiconductor field effect transistor (MOSFET), bipolar transistor, junction field effect transistor (JFET), and the like. The resistor 122 may be used to provide a voltage signal to the ADC 106 that is representative of the light intensity received by the at least one light sensor 120. Resistors 142 and 144 limit the currents through the LEDs 116 and 118, respectively. It is contemplated and within the scope of this disclosure that Green and Yellow-Green light sources may be used in combination with and/or in place of the Red and Infrared light sources. A plurality of light sources may be used and are contemplated herein. A communications interface 150 may be provided in the microcontroller for communicating with external displays and controls.

The analog brightness control 102 may comprise a first digital-to-analog converter (DAC) 130, a first buffer amplifier 132, a second DAC 134 and a second buffer amplifier 136. The digital LED control 104 may comprise a pseudo-random noise generator 138 and a clock or timing source 140. The outputs of the DACs 130 and 134 may be coupled to buffer amplifiers 132 and 136, respectively, e.g., unity gain operational amplifiers, and used to control the voltage on the collectors (or drains if using FETs) of the switches (transistors) 124 and 126, which in turn control how bright the LEDs 116 and 118 are when the DC voltages from the buffer amplifiers 132 and 136, respectively, are applied when each respective switch 124 or 126 is turned on.

Figure 2:
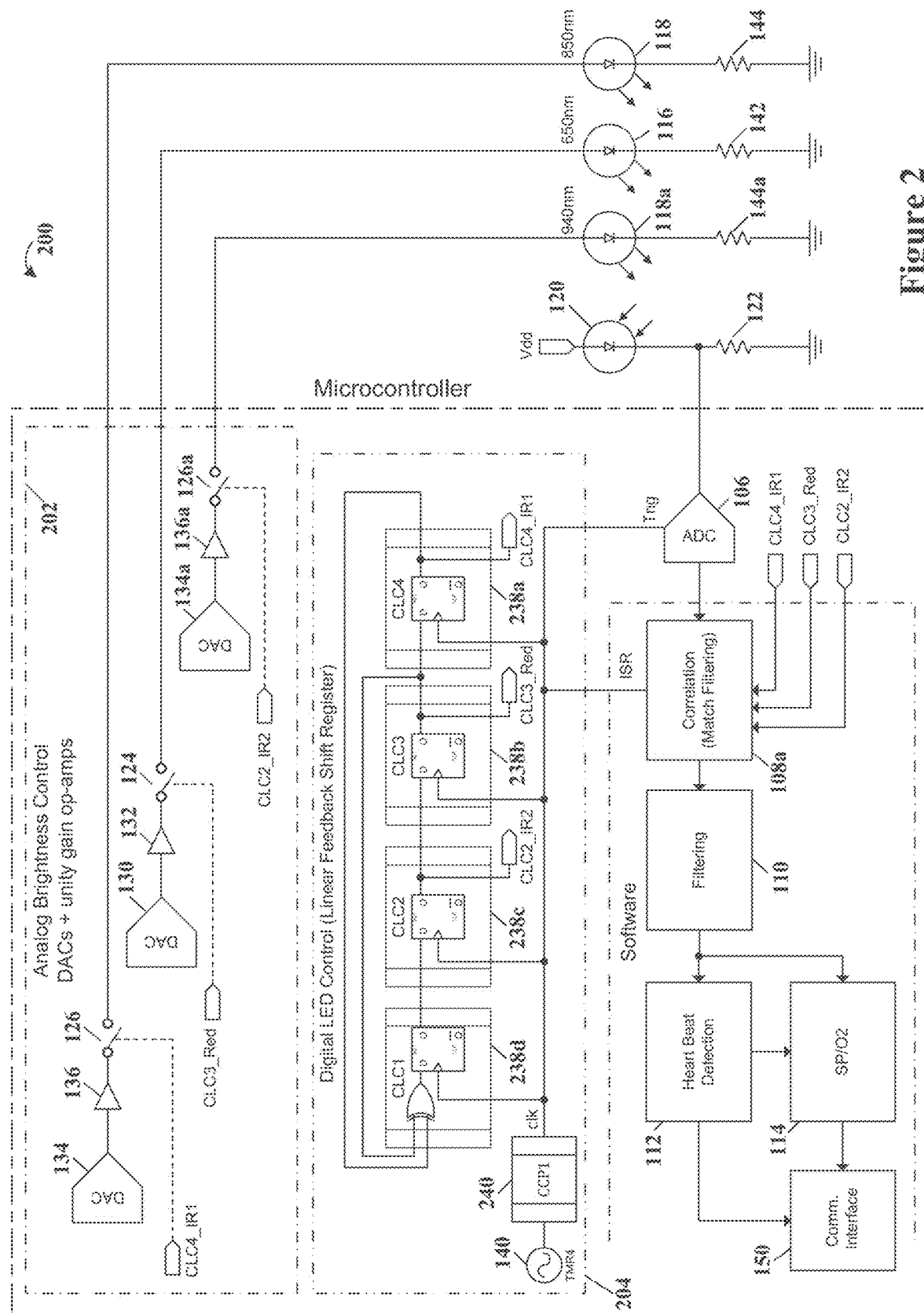
FIG. 2 illustrates a schematic block diagram of a pulse oximetry measurement system using PDM, according to another specific example embodiment of this disclosure.

The clock or timing source 140 may be used to drive the hardware or software based pseudo-random noise (PN) generator 138. The pseudo-random noise generator 138 may have one or more outputs that may be coupled to the bases (or gates) of the switches (transistors) 124 and 126. The property of a maximum length (ML) sequence generates (e.g., by a linear feedback shift register) code that sums up to $(2^n)-1$ when correlated in phase, where n is the number of flip-flops or bits in a shift register 238 as shown in FIG. 2. When out of phase, the correlation=−1. Coherent noise is exponentially reduced. White noise may be reduced by averaging. Multiple sensors may use the same code at different phases (e.g., PDM) to measure multiple signals simultaneously. A phase that isn't tied to a sensor may be used to measure background noise and then may be subtracted from the other sensor measurements.

Referring now to FIG. 2, depicted is a schematic block diagram of a pulse oximetry measurement system using PDM, according to another specific example embodiment of this disclosure. The pulse oximetry measurement system using PDM, generally represented by the numeral 200, may comprise analog brightness control 202, digital LED control 204, an analog-to-digital converter (ADC) 106, a correlation circuit (match filtering) 108a, digital filtering 110, e.g., finite impulse response (FIR) and/or infinite impulse response (IIR) filters; heartbeat detection 112, and oxygen saturation determination (SpO$_2$) 114. The aforementioned elements may be provided with an analog/digital mixed signal integrated circuit, e.g., a microcontroller. The pulse oximetry measurement system 200 may further comprise at least one red light source (e.g., Red LED) 116, at least one infrared light source (e.g., IR LED) 118, 118a, at least one light sensor (e.g., photodiode, phototransistor) 120, a current sensing resistor 122, and switches 124 and 126, e.g., metal oxide semiconductor field effect transistor (MOSFET), bipolar transistor, junction field effect transistor (JFET), and the like. The resistor 122 may be used for providing a voltage signal to the ADC 106 that is representative of the light intensity received by the at least one light sensor 120. Resistors 142, 144 and 144a limit the currents through the LEDs 116, 118 and 118a, respectively. It is contemplated and within the scope of this disclosure that Green and Yellow-Green light sources may be used in combination with and/or in place of the Red and Infrared light sources. A plurality of light sources may be used and are contemplated herein. A communications interface 150 may be provided in the microcontroller for communicating with external displays and controls.

The analog brightness control 102 may comprise a first digital-to-analog converter (DAC) 130, a first buffer amplifier 132, a second DAC 134, a second buffer amplifier 136, a third DAC 134a, and a third buffer amplifier 136a. The digital LED control 204 may comprise a pseudo-random noise generator comprising shift registers 238 and a clock source 140. The outputs of the DACs 130,134 and 134a may be coupled to buffer amplifiers 132, 136 and 136a, respectively, e.g., unity gain operational amplifiers, and used to control the voltage on the collectors (or drains if using FETs) of the switches 124, 126 and 126a, which in turn control how bright the LEDs 116, 118 and 118a are when the DC voltages from the buffer amplifiers 132, 136 and 136a, respectively, are applied when each respective switch 124, 126 or 126a is turned on. A capture compare pulse width modulation (CCP) module 240 (e.g., PDM) may provide phase control for triggering the ADC 106.

The digital LED control 204 may comprise a clock or timing source 140 that may be used to drive a pseudo-random noise (PN) generator implemented as a linear feedback shift register (LFSR) and comprising shift registers 238a, 238b, 238c and 238d that produce a maximum length sequence (ML) sequence code. The same signals that control the switching of the LEDs may also be used to correlate the ADC 106 conversion results. This allows the measurements to be effectively taken simultaneously. This method may use a pair of pseudo-random noise codes (PN codes) to stimulate one to many LEDs or other sensors. Measurements of the LEDs are effectively "simultaneous," as well as ambient light measurements. Pseudo-random measurements of IR and Red LEDs eliminate sequence biasing and the problem of flickering background lights. Motion is not removed with short PN codes, but may be eliminated by using longer PN codes.

Figure 3:
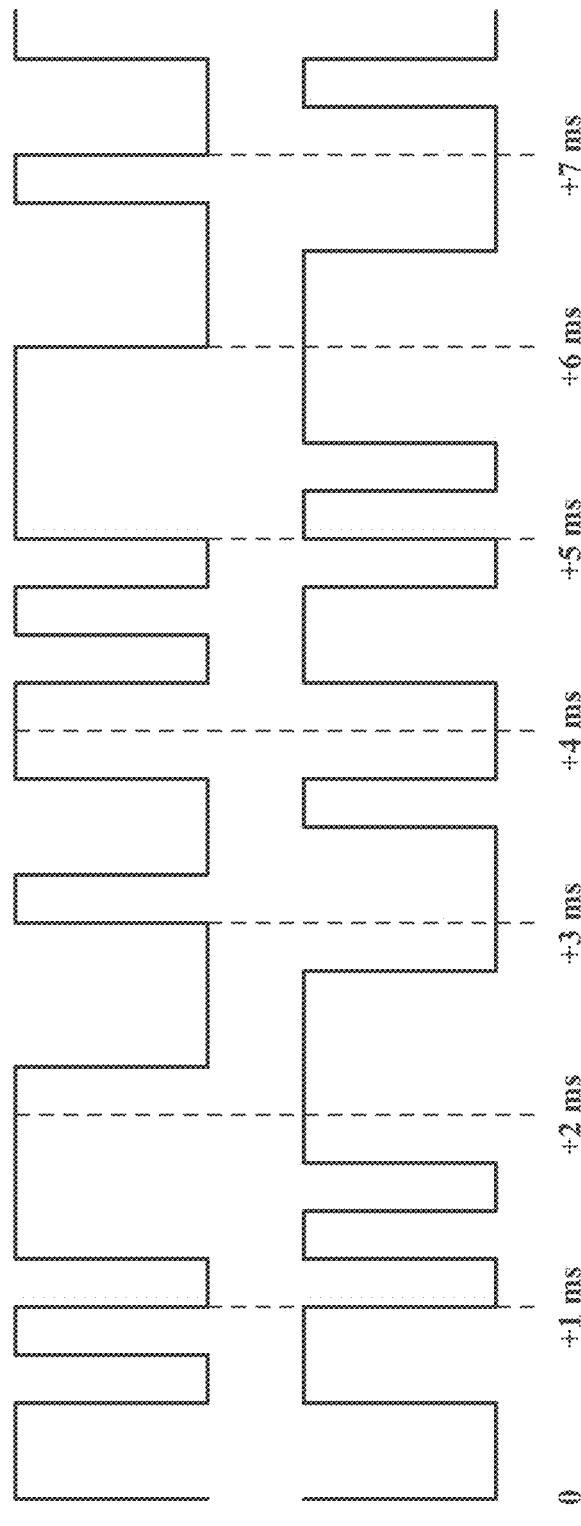
FIG. 3 illustrates a schematic timing diagram for the pulse oximetry measurement system shown in FIG. 2.

There is also one position of the LFSR that may be correlated but is not used to switch on a light source (LED). This may be used to get a measurement of the ambient light or background noise that may then be subtracted from the other two light source (red and IR) measurements. The PN sequence must repeat deterministically. FIG. 3 shows an exemplary timing diagram of control signals for the Red and IR LEDs. The PN sequence is shown for the Red and IR LEDs. The pattern may take just under 4 milliseconds to repeat, and measurements are effectively taken for red, IR and ambient light over the course of the same approximately 3.75 millisecond period. Subtraction of this background noise is optional as the correlation already diminishes the background/ambient noise significantly.

The pseudo-random noise generator (shift registers 238) may have one or more outputs that may be coupled to the bases (or gates) of the transistors 124 and 126. A maximum length (ML) sequence is a type of pseudorandom binary sequence. The properties of the ML sequence, e.g., generated by a linear feedback shift register 238, are when correlated in phase, sum up to $(2^n)-1$, where n is the number of flip-flops or bits in the shift register 238. When out of phase, the correlation=−1. Coherent noise is exponentially reduced. White noise is reduced by averaging. Multiple sensors may use the same code at different phases (PDM) to measure multiple signals simultaneously. A phase that isn't tied to a sensor may be used to measure background noise and then be subtracted from the other sensor measurements. The generated ML sequence is provided by the ML sequence. For example, using a three (3) bit LFSR the ML sequence may be 1, 1, 1, −1, 1, 1, −1.

In phase:

| Reference | * | Signal | = | Product |
|---|---|---|---|---|
| 1 | * | 1 | = | 1 |
| 1 | * | 1 | = | 1 |
| 1 | * | 1 | = | 1 |
| −1 | * | −1 | = | 1 |
| −1 | * | −1 | = | 1 |
| 1 | * | 1 | = | 1 |
| −1 | * | −1 | = | 1 |
| | | Sum: | | 7 |

Where n=3 and $2^n-1=7$. If one of the above columns is shifted up or down (with wrap-around), the products become out of Phase:

Out of phase:

| Reference | * | Signal | = | Product |
|---|---|---|---|---|
| 1 | * | −1 | = | −1 |
| 1 | * | 1 | = | 1 |
| 1 | * | 1 | = | 1 |
| −1 | * | 1 | = | −1 |
| −1 | * | −1 | = | 1 |
| 1 | * | −1 | = | −1 |
| −1 | * | 1 | = | −1 |
| | | Sum: | | −1 |

Regardless of LFSR length, the result when the two columns are out of phase with each other will always be −1. Since there cannot be a negative light, the results may be represented as:

In Phase:

| Reference | * | Signal | = | Product |
|---|---|---|---|---|
| 1 | * | 1 | = | 1 |
| 1 | * | 1 | = | 1 |
| 1 | * | 1 | = | 1 |
| −1 | * | 0 | = | 0 |
| −1 | * | 0 | = | 0 |
| 1 | * | 1 | = | 1 |
| −1 | * | 0 | = | 0 |
| | | Sum: | | 4 |

Where $2^{(n-1)}=4$

Out of phase:

| Reference | * | Signal | = | Product |
|---|---|---|---|---|
| 1 | * | 0 | = | 0 |
| 1 | * | 1 | = | 1 |
| 1 | * | 1 | = | 1 |
| −1 | * | 1 | = | −1 |
| −1 | * | 0 | = | 0 |
| 1 | * | 0 | = | 0 |
| −1 | * | 1 | = | −1 |
| | | Sum: | | 0 |

In this case, the sum when out of phase will always be 0.

The ADC 106 as shown in FIGS. 1 and 2 may be triggered using hardware logic or software programming at any point in time except at the active edge for the PN generator (shift registers 238). The ADC 106 may be triggered one or more times per clock period. As shown in FIG. 2, the same clock source 140 may be used for both the ADC 106 and the PN generator (shift registers 238). The ADC 106 may be triggered on the positive edge and the PN generator may be triggered on the negative edge of the clock signal. The CCP module 240 provides for phase control over when the ADC 106 is triggered relative to when the LFSR shift registers 238 are shifted.

For correlation, each ADC sample may be duplicated into n+1 shift registers (where n is the number of active sensors or LEDs). Each shift register is either added to or subtracted from, based upon the corresponding output of the PN generator. That is, if LED1 is on, and LED2 is off, the LED1Reg=previousLED1Reg+ADCSamp, and LED2Reg=previousLED2Reg−ADCSamp. After some number of full repetitions of the PN code, the shift registers may be read and then zeroed by the application software. This may also be done in hardware with the appropriate architecture. The correlation circuit (match filtering) 108 and 108a checks if the referenced (LED) is on, then adds if it is, and subtracts if the LED is off. Example coding is shown as follows. One having ordinary skill in the art of software coding and having the benefit of this disclosure could write different code that accomplishes the same purpose, and is contemplated herein.

```
// Add when LED is on, subtract when LED is off
#define CS_Correlate(sample, reference)            \
    ((1 == (reference)) ? (sample) : -(sample))
// total samples accumulated
static uint16_t CS_sampleCount;
// samples to accumulate for each correlation
static uint16_t CS_sampleMax = 30;
// Called whenever an ADC conversion is completed
static void CS_AdcCallback(void) {
    if (CS_sampleMax > CS_sampleCount) {
        // Read ADC sample
        adc_result_t rawSample = ADC_GetConversionResult( );
        // Correlate adc sample with LFSR taps
        CS_accumulatorRed += CS_Correlate(rawSample, redTap);
        CS_accumulatorIR1 += CS_Correlate(rawSample, ir1Tap);
        CS_accumulatorIR2 += CS_Correlate(rawSample, ir2Tap);
        CS_accumulatorBkg += CS_Correlate(rawSample, bkgTap);
        // Count number of samples correlated so far.
        CS_sampleCount++;
    } else {
        // Stop correlation when done
        bool err = CS_CorrelationStop( );
        E_ASSERT(false == err);
    }
}
```

Digital filtering may be used for additional filtering to smooth out the signal response and remove DC components if necessary. These digital filters may be any combination of FIR and/or IIR DSP elements, as known by those having ordinary skill in the digital filter arts and having the benefit of this disclosure.

For heartbeat detection, any method may be used. A software phase-locked-loop (PLL) may be used for implementation of heartbeat detection, or a state machine representation may also be used. The peak-to-peak signal output from the LEDs may be measured over the period of each heartbeat. These values can be further filtered, and the ratio of IR/Red or Green/Yellow-Green light intensities may be used in determining oxygen saturation levels ($SP/O_2$).

Figure 4:
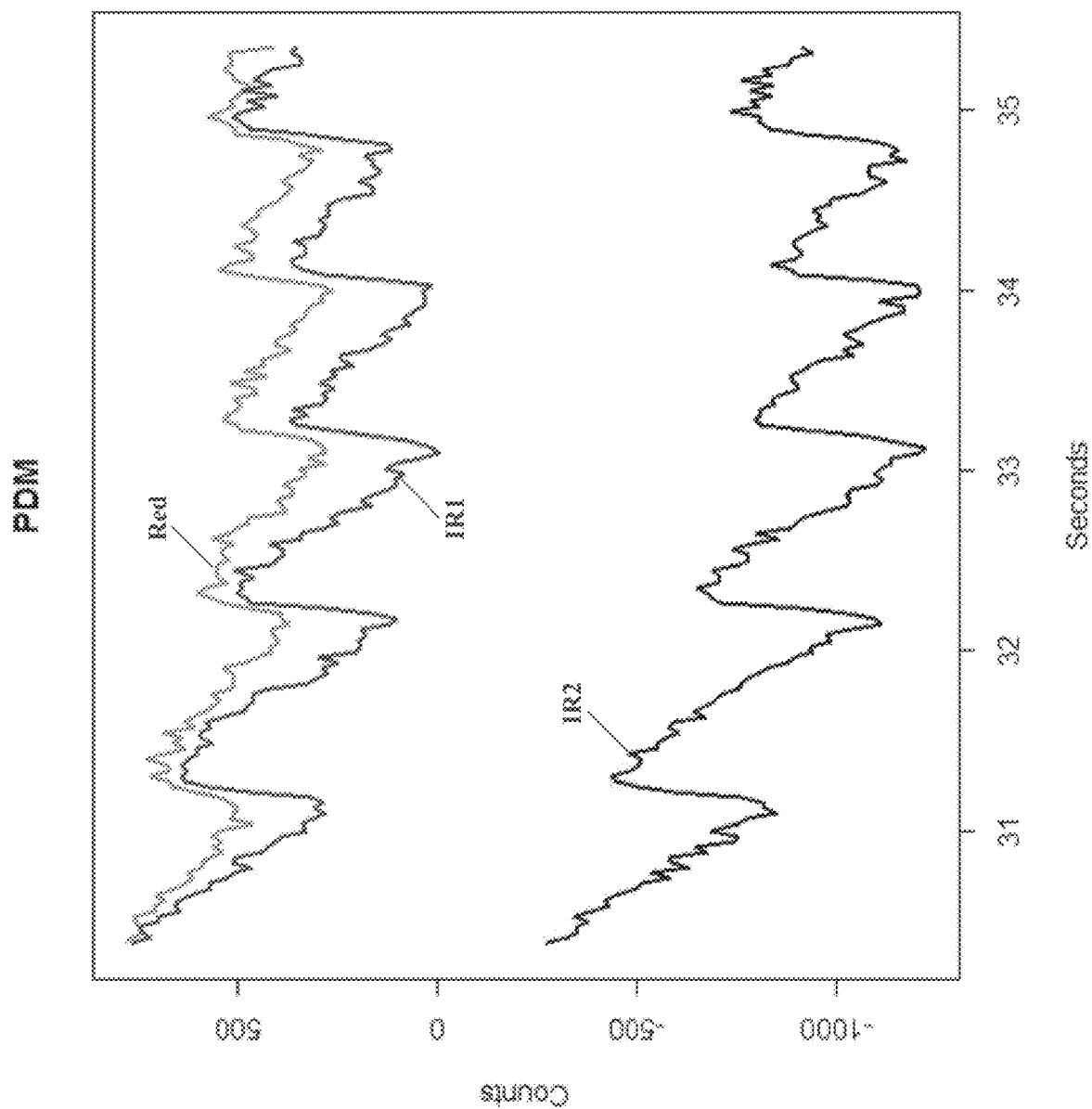
FIG. 4 illustrates exemplary waveforms of the pulse oximetry measurement systems shown in FIGS. 1 and 2, according to the teachings of this disclosure.
Figure 5:
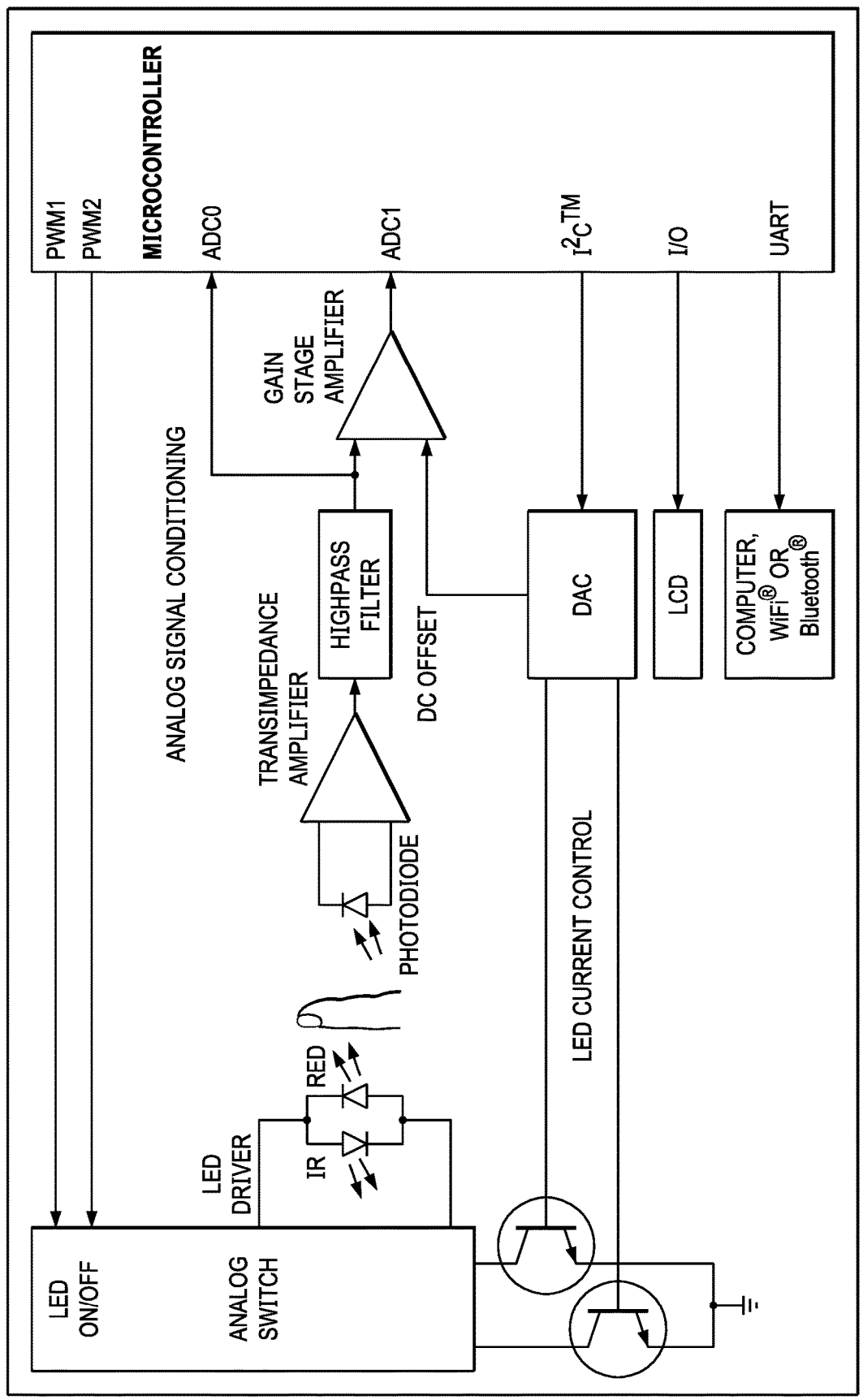
FIG. 5 illustrates a schematic block diagram of a general overview of a prior technology pulse oximetry measurement system.
Figure 6:
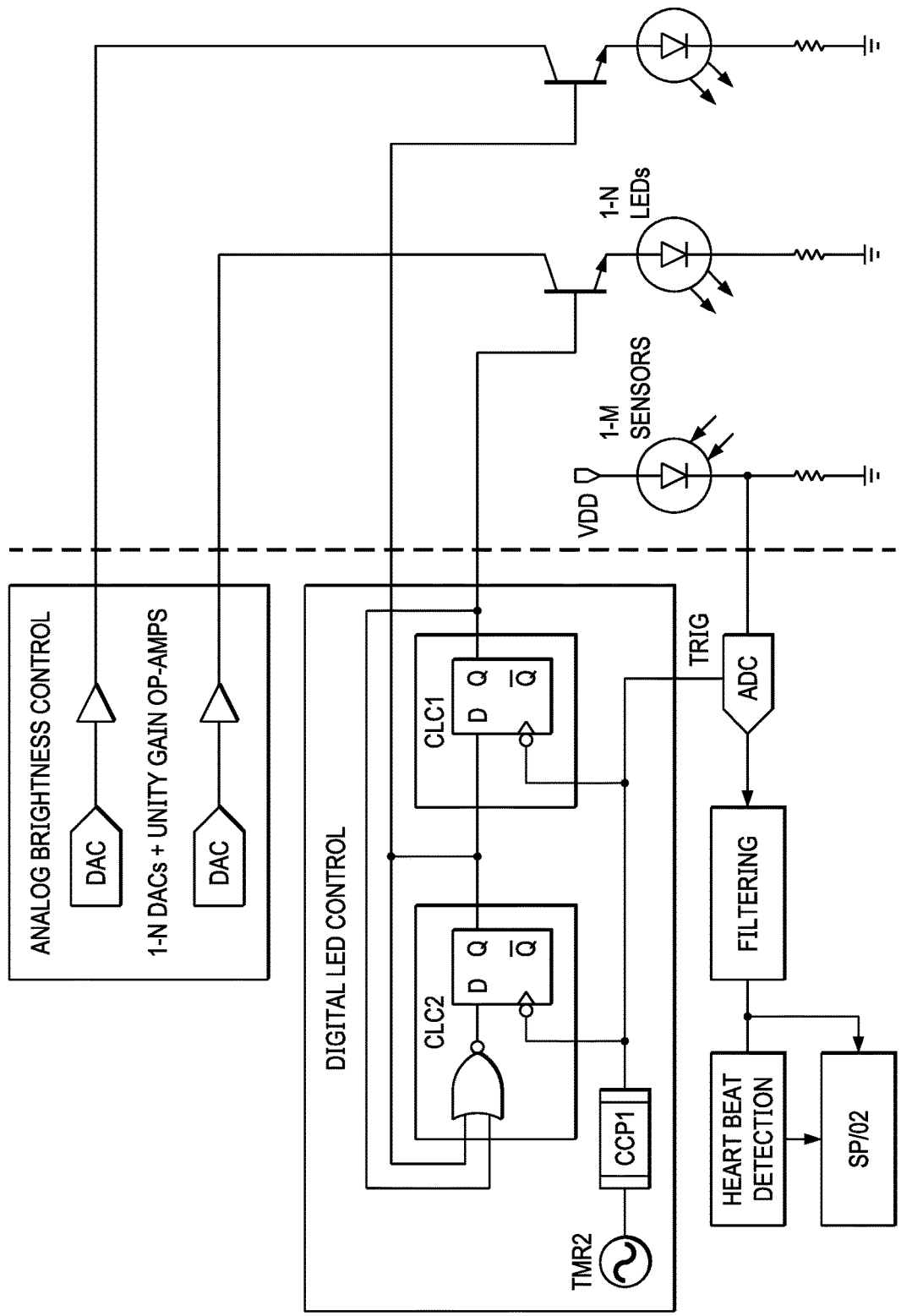
FIG. 6 illustrates a more detailed schematic block diagram of a prior technology pulse oximetry measurement system.

FIG. 4 shows exemplary waveforms displaying the pulse signals according to various embodiments. The waveforms shown in FIG. 4 are taken at the output of the correlation (match filter) 108 before any digital filtering 110 is applied thereto. These waveforms provide for a superior signal range, even before subsequent filtering, compared to the prior technology signal range that has been filtered and is shown in FIG. 7. In summary, signal generation may be provided in hardware, for example using the configurable logic circuits available in PIC microcontrollers such as the PIC16F1778. Filtering arithmetic requires only adding and subtracting. A communications interface (not shown) may be coupled to or part of the microcontroller and provide oxygen saturation and heartbeat information to a display and/or computer (not shown).

It is contemplated and within the scope of this disclosure that the signal analysis as discussed hereinabove using a pseudo-random noise generator is not restricted to pulse oximeter measurement but may also apply to other sensor signal evaluations that require a driving signal to produce a measurement signal. Hence, the method as proposed herein may apply to various other sensor signal evaluation systems and methods.

The invention claimed is:

1. A system for measuring multiple signals in a body, said system comprising:
    at least one first light source generating a first color light;
    at least one second light source generating a second color light;
    at least one light sensor adapted for detecting light amplitudes, wherein the at least one first and second light sources and the at least one light sensor are adapted for a portion of a body to be located therebetween;
    a pseudo-random noise generator adapted for generating a pseudo-random control sequence for turning on and off the at least one first and second light sources at pseudo-random times, wherein the control sequence for the first and second light source use a same code, wherein the code fed to the second light source is phase shifted with respect to the code fed to the first light source;

an analog-to-digital converter (ADC) for converting sampled light amplitudes from the at least one light sensor into digital representations thereof; and a correlation circuit coupled to a digital output of the ADC and the pseudo-random noise generator, wherein the correlation circuit associates the digital representations with corresponding ones of the at least one first and second light sources, wherein the pseudo-random noise generator comprises a linear feedback shift register and the pseudo-random control sequence comprises a maximum length (ML) sequence, wherein each of the linear feedback shift register and the ADC receive a clock signal, and wherein the ADC is triggered on a positive going edge of the clock signal and the pseudo-random noise generator is triggered on a negative going edge of the clock signal.

2. The system according to claim 1, further comprising a digital filter for filtering the correlated digital representations.

3. The system according to claim 2, further comprising a heartbeat detection circuit coupled to an output of the digital filter.

4. The system according to claim 2, further comprising a blood oxygen saturation ($SpO_2$) determination circuit coupled to an output of the digital filter.

5. The system according to claim 1, wherein the ML sequence is phase shifted for each one of a plurality of other light sources.

6. The system according to claim 1, wherein the linear feedback shift register comprises a plurality of shift registers that are either added to or subtracted from based upon a corresponding output of the pseudo-random noise generator.

7. The system according to claim 1, further comprising:
at least one first digital-to-analog converter (DAC) having an analog output coupled to the at least one first light source; and
at least one second digital-to-analog converter (DAC) having an analog output coupled to the at least one second light source;
wherein the at least one first and second DACs control light intensities of the first and second light sources.

8. The system according to claim 1, wherein the first color light is at a red wavelength and the second color light is at an infrared wavelength.

9. The system according to claim 1, wherein the first color light is at a green wavelength and the second color light is at a yellow-green wavelength.

10. The system according to claim 1, wherein digital representations of ambient light samples are subtracted from the digital representations of the sampled light amplitudes from the at least one first and second light sources.

11. The system according to claim 1, wherein interfaces for the at least one first and second light sources and the at least one light sensor, the pseudo-random noise generator, ADC, and correlation circuit are provided by a microcontroller.

12. The system according to claim 11, further comprising a communications interface coupled to the microcontroller and providing oxygen saturation and heartbeat information.

13. The system according to claim 1, wherein the at least one first and second light sources comprise light emitting diodes (LEDs) and the at least one light sensor comprises at least one photo-diode or photo-transistor.

14. A method for measuring multiple signals in a body, said method comprising the steps of:
generating a first color light with at least one first light source;
generating a second color light with at least one second light source;
detecting light amplitudes with at least one light sensor, wherein the at least one first and second light sources and the at least one light sensor are adapted for a portion of a body to be located therebetween;
turning on and off the at least one first and second light sources at pseudo-random times generated by a pseudo-random noise generator generating a pseudo-random control sequence, wherein the control sequence for the first and second light source use a same code, wherein the code fed to the second light source is phase shifted with respect to the code fed to the first light source;
converting sampled light amplitudes from the at least one light sensor into digital representations thereof with an analog-to-digital converter (ADC); and
correlating the digital representations of the sampled light amplitudes with corresponding ones of the at least one first and second light sources using the pseudo-random times from the pseudo-random noise generator,
wherein the pseudo-random noise generator comprises a linear feedback shift register and the pseudo-random control sequence comprises a maximum length (ML) sequence, wherein each of the linear feedback shift register and the ADC receive a clock signal, and wherein the ADC is triggered on a positive going edge of the clock signal and the pseudo-random noise generator is triggered on a negative going edge of the clock signal.

15. The method according to claim 14, further comprising the step of filtering the correlated digital representations with a digital filter.

16. The method according to claim 14, further comprising the step of determining oxygen saturation ($SpO_2$) of blood from the digital representations of the sampled light amplitudes.

17. A microcontroller configured for measuring multiple signals in a body, comprising:
at least one first driver for turning on and off at least one first light source generating a first color light;
at least one second driver for turning on and off at least one second light source generating a second color light;
at least one analog input for receiving an output from at least one light sensor adapted for detecting light amplitudes, wherein the at least one first and second light sources and the at least one light sensor are adapted for a portion of a body to be located therebetween;
a pseudo-random noise generator adapted for generating a pseudo-random control sequence for turning on and off the at least one first and second light sources at pseudo-random times, wherein the control sequence for the first and second light source use a same code, wherein the code output by the second driver for the second light source is phase shifted with respect to the code output by the first driver for the first light source;
an analog-to-digital converter (ADC) for converting sampled light amplitudes received from the at least one light sensor into digital representations thereof; and a correlation circuit coupled to a digital output of the ADC and the pseudo-random noise generator, wherein the correlation circuit associates the digital representations with corresponding ones of the at least one first and second light sources, wherein the pseudo-random noise generator comprises a linear feedback shift register and the pseudo-random control sequence comprises a maximum length (ML) sequence, wherein each of the linear feedback shift register and the ADC receive a clock signal, and wherein the ADC is triggered on a positive going edge of the clock signal and the pseudo-random noise generator is triggered on a negative going edge of the clock signal.

18. The microcontroller according to claim 17, further comprising:

at least one first digital-to-analog converter (DAC) coupled to at least one first analog output adapted for coupling to the at least one first light source; and at least one second digital-to-analog converter (DAC) coupled to at least one second analog output adapted for coupling to the at least second light source;

wherein the at least one first and second DACs control intensities of the first and second color lights.

19. The microcontroller according toto claim 17, wherein the linear feedback shift register has a plurality of outputs each representing a different shift stage and wherein the at least one first driver is coupled with a different output of the linear feedback shift register than the second driver.

* * * * *